United States Patent [19]
Rinner

[11] Patent Number: 6,017,342
[45] Date of Patent: Jan. 25, 2000

[54] COMPRESSION AND DISTRACTION INSTRUMENT

[75] Inventor: James A. Rinner, Racine, Wis.

[73] Assignee: Beere Precision Medical Instrumnets, Inc., Racine, Wis.

[21] Appl. No.: 09/129,514

[22] Filed: Aug. 5, 1998

[51] Int. Cl.[7] .................................................. A61B 17/56
[52] U.S. Cl. ........................................................ 606/57
[58] Field of Search .............................. 606/55, 57, 105, 606/58; 600/218, 219, 222

[56] References Cited

U.S. PATENT DOCUMENTS

| | | | |
|---|---|---|---|
| 2,002,021 | 5/1935 | Rouse . | |
| 4,102,339 | 7/1978 | Weber et al. . | |
| 4,271,836 | 6/1981 | Bacal et al. . | |
| 4,502,475 | 3/1985 | Weigle et al. . | |
| 4,898,161 | 2/1990 | Grundei . | |
| 5,297,538 | 3/1994 | Daniel | 606/207 |
| 5,755,661 | 5/1998 | Schwartzman | 600/219 |
| 5,885,210 | 3/1999 | Cox | 600/219 |
| 5,899,901 | 5/1999 | Middleton | 606/105 |

OTHER PUBLICATIONS

Beere Precision Medical Instruments, Inc. 1998 Catalog (One Sheet).

*Primary Examiner*—Gene Mancene
*Assistant Examiner*—Eduardo C. Robert
*Attorney, Agent, or Firm*—Arthur J. Hansmann

[57] ABSTRACT

A compression and distraction instrument having two pivotally connected handles. Jaw portions engage objects, such as human bone, for purposes of maneuvering. A control screw connects with the handles, through a mechanical advantage arrangement, and the screw pivots the jaw portions for the engagement of the objects. There is an anti-friction connection between the screw and the handles, for accurate and precise movement of the jaws. In one embodiment, the screw is axial of the instrument, and, in the other embodiment, the screw is transverse thereto, both have mechanical advantage.

27 Claims, 5 Drawing Sheets

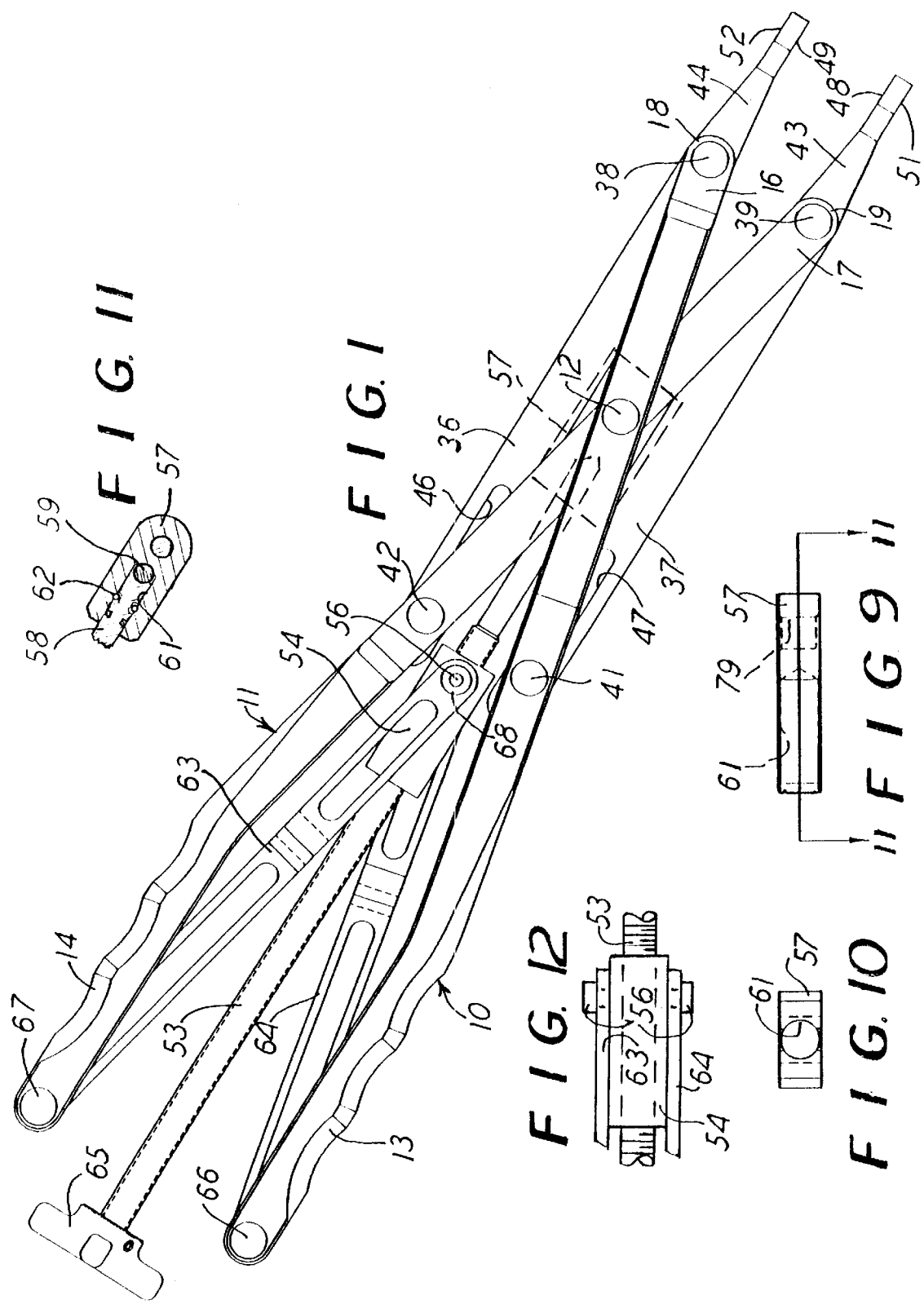

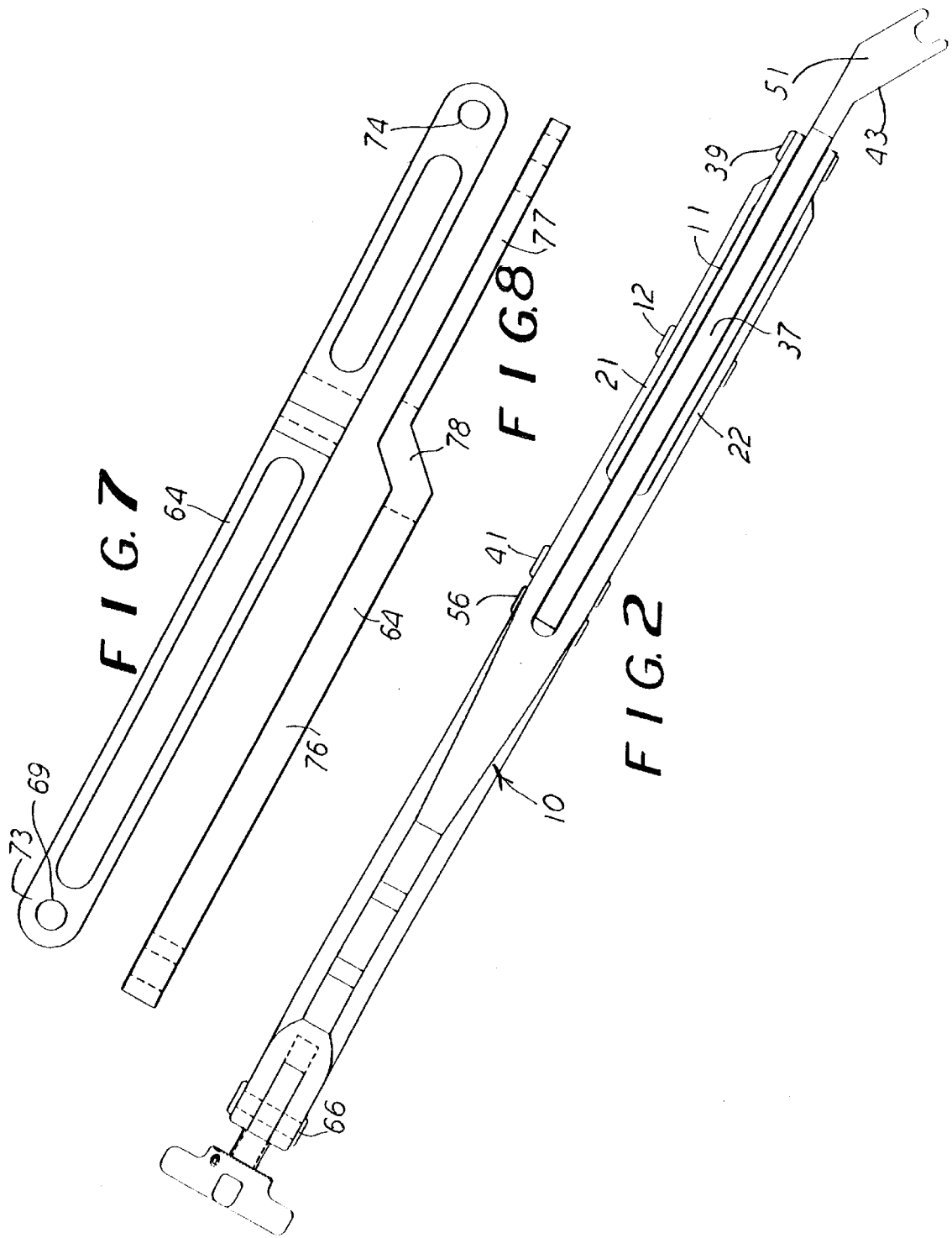

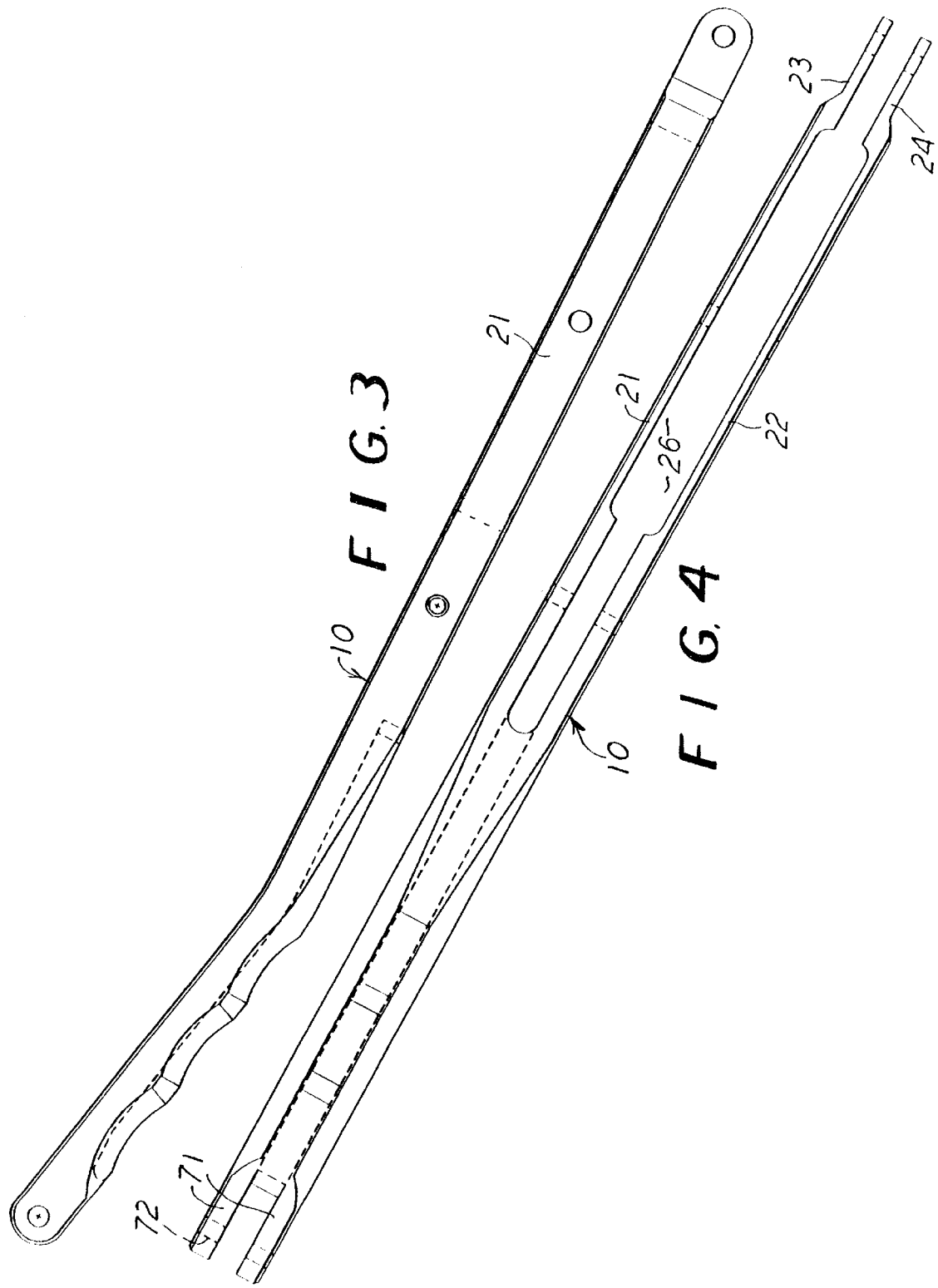

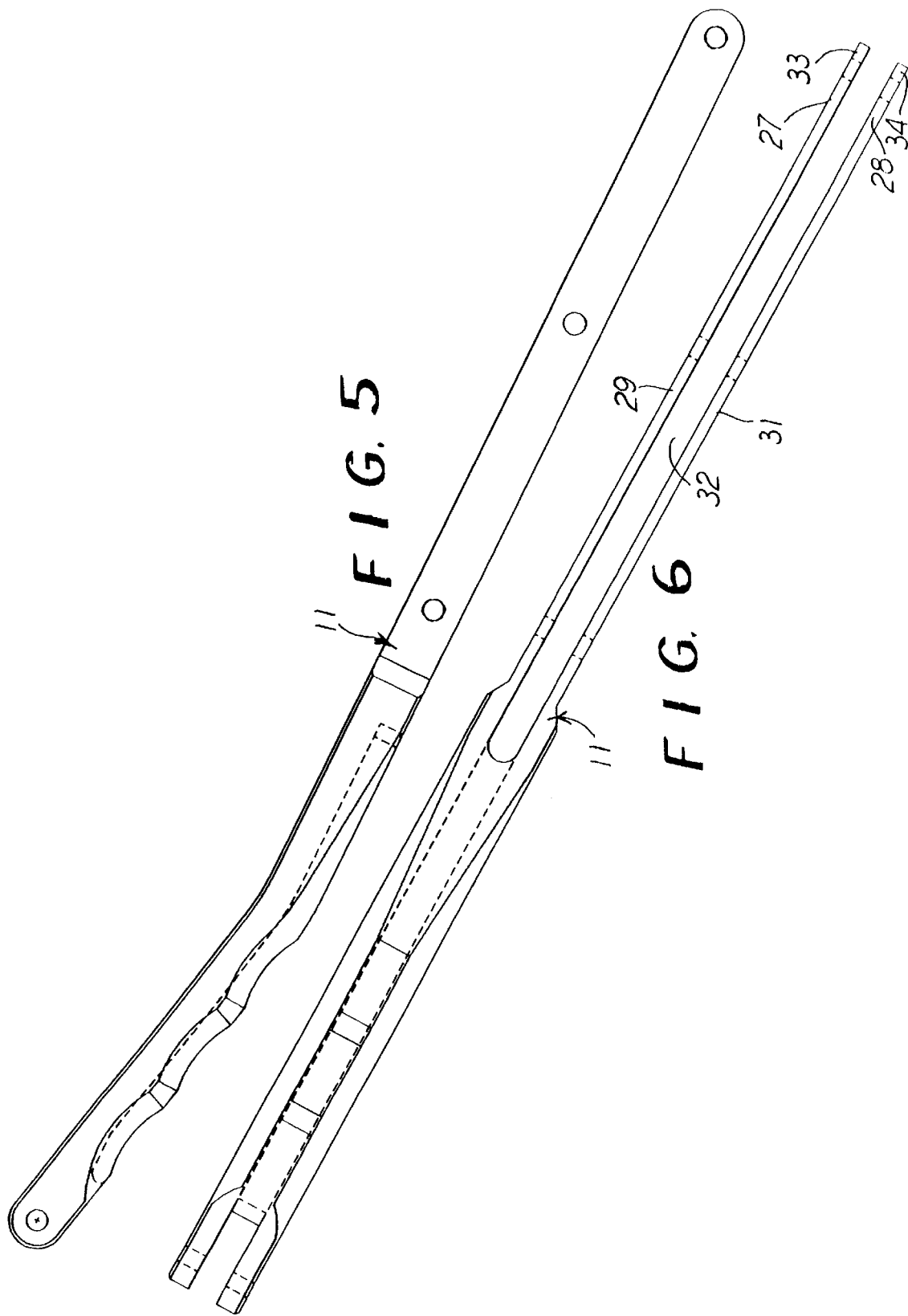

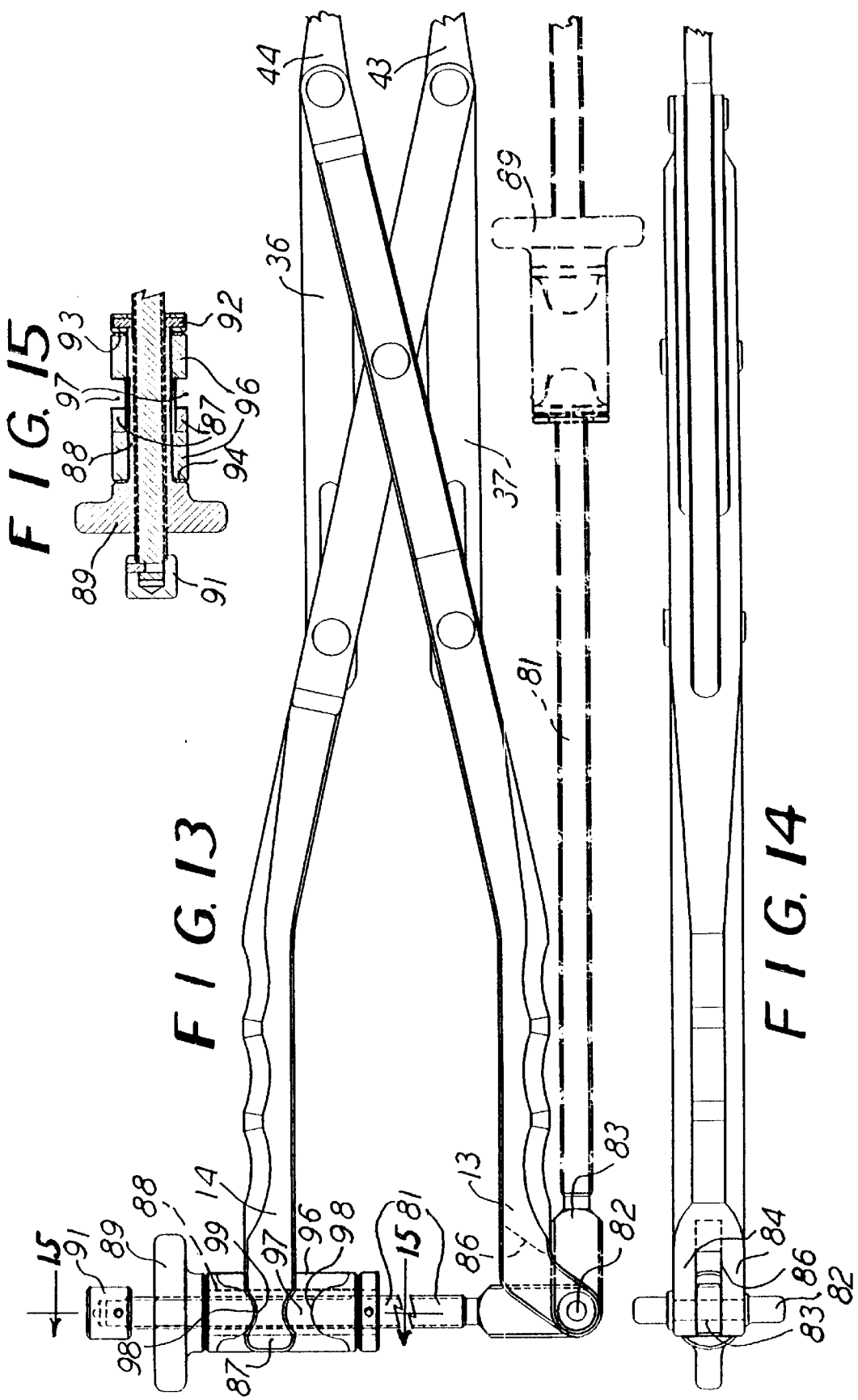

COMPRESSION AND DISTRACTION INSTRUMENT

This invention relates to a compression and distraction instrument which is useful in manipulating bones in a human, particularly in manipulating the spine of a person, such as in surgical procedures. Such manipulation may occur through direct contact by the instrument with bone or devices attached to the bone, such as implants.

BACKGROUND OF THE INVENTION

This invention is more than, arid thereby different from, instruments which individually either compress or expand the spinial bones, for instance. The prior art cited in this instance discloses instruments or tools which individually can manipulate bones, such as by extension or compression thereof.

The present invention improves upon the known instruments in that it provides an instrument for compression and distraction of bones, and it does so with an instrument which is arranged with a mechanical advantage of a nature which produces universal, that is, complete, variations in the instruments working jaws which are in contact with the bones. More specifically, there is no incremental, or step-by-step positioning of the jaws, but, instead, the jaws are smoothly and infinitely positionied in maneuvering of the jaws.

Accordingly, it is an object of this invention to provide a compression and distraction instrument for use in the medical field and to have the instrument operative under a mechanical advantage and in a smooth and continuous operation whereby the working jaws are smoothly and uniformly positioned for compression and distraction.

Accordingly, the instrument of this invention accomplishes the aforementioned and it does so by means of jaw surfaces which remain parallel to each other in both the compression and distraction function and while the jaws are moved toward and away from each other in a uniform or smooth movement.

A screw connects to two pivotal handles, and there is an anti-friction connection therebetween. One embodiment has the screw disposed longitudinally of the instrument, and the other embodiment has the screw pivoted to the handle for connection,

BRIEF DESCRIPTION OF THE DRAWINGS

FIG. 1 is a top plan view of an instrument of this invention.

FIG. 2 is a right side elevational view of FIG. 1.

FIG. 3 is an enlarged top plan view of the right handle of FIG. 1, but shown by itself.

FIG. 4 is a right side view of FIG. 3.

FIG. 5 is an enlarged bottom view of the left handle shown in FIG. 1, but by itself.

FIG. 6 is a side view of FIG. 5.

FIG. 7 is an enlarged top view of a lever in FIG. 1.

FIG. 8 is a side view of FIG. 7.

FIG. 9 is a top view of a nut useful in FIG. 1.

FIG. 10 is an end elevational view of FIG. 9.

FIG. 11 is a sectional view taken on plane 11—11 of FIG. 9.

FIG. 12 is a side elevational view of a fragment of FIG. 1.

FIG. 13 is a top plan view of another embodiment of this invention, fragmentarily shown.

FIG. 14 is a side elevational view of FIG. 13.

FIG. 15 is a sectional view along the plane 15—15 of FIG. 13.

DETAILED DESCRIPTION OF THE PREFERRED EMBODIMENTS

FIGS. 1 and 2 show the assembly of the instrument of this invention, and it includes the right-hand handle 10 and the left-hand handle 11 which are pivotally joined together by the center pivot pin 12 extending through the two handles. It will be seen that the handles 10 and 11 have hand grip portions 13 and 14, respectively, and the handles are elongated, from the left to right, as viewed in FIGS. 1 and 2. Also, the handles 10 and 11 have respective jaw portions 16 and 17. Accordingly, it will be seen and understood that upon moving the hand grip portions 13 and 14 toward and away from each other, the jaw portions 16 and 17 likewise move toward and away from each other.

Also, the jaw portions 16 and 17 have terminal ends 18 and 19, respectively, which extend away from the pivot 12, relative to the hand grips 13 and 14. The portions 18 and 19 are designated as being at the extreme terminal and distal ends of the handles 10 and 11.

FIGS. 2, 4, and 6 show that the respective handles 10 and 11 are bifurcated along their lengths and the handle 10 has two spaced-apart legs 21 and 22 which extend for substantially one-half the total length of the handle 10 and which terminate in closer spaced end portions 23 and 24, and those portions 23 and 24 are the handle jaw portions 16 and 18 mentioned above. Thus, the handle 10 has a longitudinal space 26, as seen in FIG. 4.

FIGS. 5 and 6 show the handle portion 11 which has its jaw portion 17 presented in the terminal ends 27 and 28 of two spaced-apart legs 29 and 31. That arrangement presents a space 32 between the legs 29 and 31 and it also presents the distal or terminal ends 33 and 34, relative to the pivot 12.

With the arrangement shown and described in regard to handles 10 and 11, it will be understood that the handles are pivoted together by means of the pivot pin 12, and they are nested together with the handle legs 29 and 31 extending between the legs 21 and 22, as seen in FIG. 2.

As shown in FIGS. 1 and 2, two additional jaw members 36 and 37 are interconnected with the handles 10 and 11 by means of pivot pins 38, 39, 41, and 42. The members 36 and 37 are substantially planar in their extent, except for an angulated finger portion 43 and 44, both of which extend beyond the respective terminal ends 18 and 19 of the handles.

It will be seen and understood that the jaw members 36 and 37 are attached to the handles 10 and 11 so that the members 36 and 37 always remain parallel to each other, even through the pivotal action of the handles 10 and 11, and that arrangement is achieved by means of the members 36 and 37 having slots 46 and 47 therein for slidably receiving the respective pivot pins 41 and 42.

Also, the jaw portions 43 and 44 have inwardly facing surfaces 48 and 49 which work together for the compression of the bone, and they also have the outwardly facing portions 51 and 52, for the distraction of the bone. Surfaces 48 and 49 form one pair where the surfaces remain parallel during operation, and surfaces 51 and 52 form another pair where the surfaces 51 and 52 remain parallel during operation.

For mechanical advantage and smooth and uniform action of the instrument, an elongated screw 53 is connected with an elongated nut 54 which carries pins 56. The end of the screw 53 is connected with the pivot pin 12 by means of a carrier 57 through which the pin 12 extends, and the screw end 58 extends into the carrier 57 to be anchored therewith. A ball bearing 59 is interposed between the end of the screw 53 and the base of a hole 61 in the carrier 57, for ease of turning the screw 53 against forces acting on the aforementioned jaws. A dowel pin 62 interconnects the end of the screw 53 and the carrier 57 to restrict any axial movement of the screw 53 relative to the carrier 57 when the screw 53 is pulled or turned.

Levers 63 and 64 are interconnected between the pins 56 and pins 66 and 67 on the hand grips 13 and 14. The levers are seen in FIG. 1 and also in FIGS. 7 and 8 with regard to the lever 63. Thus, it will be seen and understood, that upon rotation of the screw 537 such as by means of its handle 65, the elongated nut 54 will move along the length of the screw 53 and thus position the ends 68 of the levers 63 and 64, and thereby move the hand grips 13 and 14 either toward or away from each other in the desired actuation of the instrument for purposes of moving the jaws 43 and 44 relative to each other. In that arrangement, there is a large mechanical advantage by use of the screw 53 and the levers 63 and 64, and also, by virtue of the thread action from the screw 53, there is smooth and complete adjustment of the positioning of the jaws 43 and 44 with absolute and complete accuracy desired for medical procedures.

As seen in FIG. 1, the instrument is arranged such that the pivot connections 38 and 39, relative to the center pivot 12, are of a respective equal distance from the pivot 12 to the connections 41 and 42. Thus, the additional jaws 36 and 37 remain parallel to each other throughout the entire range of pivotal action of the handles 10 and 11. Also, to achieve the parallelism mentioned, the connections 38 and 41, relative to the center pivot 12, lie along one straight line. Likewise, the connections 39 and 42, relative to the center pivot connection 12, lie along one straight line. Of course the connections 41 and 42 will slide in the respective slots 47 and 46 during the pivot action.

The levers 63 and 64 have connection holes 69 for pivotally receiving the respective pivot connections 66 and 67 which also pivotally connect with respective handles 10 and 11. Thus, the handles 10 and 11 have a bifurcated end 71 which presents its aligned hole 72 for receiving the respective pins 66 and 67, and these spaced-apart bifurcations 71 of course receive the ends 73 of the respective levers 63 and 64. Further, the levers 63 and 64 have an opening 74 which pivotally receives the pins 56 which actually extend only on opposite sides of the connector 54 such that the then two pins 56 pivotally connect to the connector 54 and to the two ends of the levers 63 and 64 through the openings 74. Of course the nut 54 is thus non-rotatably retained, and it can therefore move axially of the screw 53 when the screw 53 is rotated.

FIGS. 7 and 8 further show that the levers 63 and 64 have two planar extents 76 and 77 which are offset from each other and are interconnected by the angulated portion 78 of each of the levers 63 and 64. With the offsets shown herein, such as 78 and 23 and 24 in FIG. 4, the entire instrument can occupy only one straight and narrow side projection, as shown in FIG. 2.

FIG. 12 shows the screw 53 in threaded relation with the nut 54, and it shows the two pivot pins 56 on opposite sides of the nut 54 and being suitably secured to the nut 54 for pivotally connecting the two levers 63 and 64 relative to the nut 54. Of course the nut 54 is internally threaded for snug, threaded engagement with the externally threaded screw 53, and thus the precision and smooth displacement of the nut 54 is achieved for the precise and accurate positioning of the gripping jaws of this instrument.

Also, FIGS. 9 and 10 show the connector 57 which has an opening 79 for pivotally receiving the center pivot post 12, and it has its opening 61 for rotatably, but non-axially movably, receiving the end of the screw 53 so that the screw 53 will rotate relative to the connector 57, and the handles 10 and 11 will pivot relative to the connector 57.

The instrument is therefore arranged for gripping the hand portions 13 and 14, say with one hands, and then actuating the screw 53 through the knob 65 with the other hand. The screw is of a fine thread so that it will accurately and easily move the nut 54. Also, the ball bearing 59 is subjected to lubricant, such as grease, which is held by the O-ring shown on the shaft 58 adjacent the dowel 62, Thus, there is anti-friction connection between the screw 53 and the handles 10 and 11 for precise and easy action once the engaging surfaces 48, 49, 51, and 52, are respectively in contact with the work-piece, such as human bone, and then the screw is actuated to press those surfaces against the bone which has been engaged. The arrangement shown is such that the screw 53 exerts a thrust upon the pivot pin 12, along the longitudinal axis of the screw 53, and thus the bearing 59 is in the nature of a thrust bearing and is of course an anti-friction bearing with the arrangement and lubrication shown and described.

FIGS. 13 through 15 show another embodiment of the invention, and it will be readily seen that this embodiment includes the same general arrangement of handles 10 and 11 and of additional jaw members 36 and 37. Also, the jaw ends 43 and 44 present their two pairs of gripping surfaces, such as the pair of surfaces 48, 49 and the pair of surfaces 51 and 52 for respective compression and distraction operation, just as in connection with the previous embodiment.

The second embodiment does not include the longitudinal screw 53, but, instead, it has a screw 81 which is pivotally connected to the modified handle 10 by means of a pivot pin 82 extending through the handle 10 and the handle end 83 affixed with the screw 81. At this time it will be seen and understood that the screw 81 can pivot from the solid line position shown in FIG. 13 to the dash line position shown therein. Thus, the handle 10 is modified to have two spaced-apart fingers 84 which present a slot 86 therebetween, and that is where the screw 81 can swing or pivot.

The screw 81 extends between the hand grip portions 13 and 14 of the two handles, and the handle 14 also has two spaced-apart fingers or portions 87, just as with the shown portions 84, and the screw 81 carries a cylindrical nut 88 which includes a knob 89, as best seen in FIG. 15. Of course the nut 88 and screw 81 are threadedly connected, and the nut 88 can rotate on the screw 81 to move axially therealong in both axial directions of the screw 81. A stop 91 is affixed to the end of the screw 81 to preclude the nut 88 from being moved off the screw 81.

A thrust washer 92 is pinned to the nut 88, and the washer 92 and the knob 89 present inwardly facing annular shoulders 93 and 94, respectively. A sleeve-type member 96 is slidably disposed on the nut 88 to move between the shoulders 93 and 94 in both directions along the axis of the screw 81. The fingers 87 flank the member 96 and they extend to opposite sides of the member 96 by extending through side openings 97 in the member 96. The member 96 and the fingers 87 present mating and matching surfaces which face each other, such as the arcuate surfaces 98 on the member 96 and which face the slot 97. The hand grip portion has its part of the matching surfaces as designated 99 which respectively face the surfaces 98 and engage those surfaces, such as in the upper engaged portion shown in FIG. 13. With that arrangement, when the upper engaged surfaces 98 and 99 are in contact with each other and nested together, such as shown, then the nut 88, through the member 96, transmits force from the screw 81 and onto the handle 14 to tend to close the handles 13 and 14 toward each other, and thus close the jaws 43 and 44 toward each other in the compression mode.

Conversely, when the knob 89 is rotated on the screw 81 to cause the nut 88 to move the member 96 upwardly, from the FIG. 13 position shown, then the handles are being separated and the instrument is placed in the distraction mode. In that arrangement, the member 96 would move upwardly to where its surface 98 engages the handle surface 99 and thus precludes rotation of the member 96 which is then only moved along the axis of the screw 81.

It will thus be seen and understood that the screw 81 carries a nut 88 which is rotatable on the screw 81 to thus move axially of the screw and move the handles toward and away from each other, as desired. Also, the screw 81, along with its nut 88 and attending parts described, can swing from the solid line position shown in FIG. 13 to the dotted line position shown therein, and thus the instrument can be placed in a compact storage position. Further, the surgeon or other user can grip either or both of the handles and can actuate the knob 89 for movement of the nut along the screw 81, as desired. The member 96 has its two arcuate surfaces 98 facing each other and they are convex. The handle fingers 87 have their two arcuate surfaces 99 facing away from each other, and they are concave. In pivoting the screw to operative connection with the handle, the side openings 97 in the member 96 permit movement of the member 96 to position it between fingers 87 and to automatically align surfaces 98 and 99 to face each other in the ready position of engagement for forcing in Other direction along the screw 81.

What is claimed is:

1. An instrument for compression and distraction of objects comprising two elongated first and second handles, a pivot pin pivotally connecting said handles together at a location intermediate the length of said handles, said handles being arranged to have hand grip portions thereon disposed to one side of said pivot pin and to have jaw portions thereon disposed to the side of said pivot pin opposite from said one side whereby said jaw portions move toward and away from each other when said handles are respectively moved toward and away from each other, said jaw portions having terminal ends extending away from said pivot pin, a first additional jaw pivotally connected to said hand grip portion of said first handle and pivotally connected to said jaw portion of said second handle, and a second additional jaw pivotally connected to said hand grip portion of said second handle and pivotally connected to said jaw portion of said first handle, and with said additional jaws extending beyond said terminal ends of said jaw portions in the direction away from said pivot pin and having gripping surfaces for gripping objects between said surfaces, said additional jaws being pivotally connected to said handles for the pivoting of said handles about said pivot pin, a screw supported relative to said pivot pin and extending between said handles, a nut threadedly mounted on said screw, and a lever pivotally connected with said nut and each of said grip portions and arranged to move said grip portions toward and away from each other upon turning of said screw.

2. The instrument for compression and distraction of objects as claimed in claim 1, wherein said additional jaws are disposed parallel to each other.

3. The instrument for compression and distraction of objects as claimed in claim 2, wherein the location of the pivot connections of said additional jaws are equally spaced from said pivot pin on opposite sides thereof and lie along a straight line which extends through said pivot pin and said connections.

4. The instrument for compression and distraction of objects as claimed in claim 3, wherein said additional jaws are arranged to have said connections in each of said additional jaws move in equal amounts of movement upon pivoting of said handles and thereby remain parallel to each other throughout the pivoting of said handles.

5. The instrument for compression and distraction of objects as claimed in claim 1, wherein said screw is rotatably connected with said pivot pin, and including a ball-bearing interposed between said pivot pin and said screw to facilitate rotation of said screw.

6. The instrument for compression and distraction of objects as claimed in claim 1, wherein said gripping surfaces of said additional jaws exist on both opposite sides of each of said additional jaws and being arranged to engage objects in response to both directions of pivot of said handles for alternate compression and distraction of said objects.

7. The instrument for compression and distraction of objects as claimed in claim 6, wherein all said gripping surfaces are parallel to each other.

8. The instrument for compression and distraction of objects as claimed in claim 1, wherein said additional jaws each have a straight slot therein for receiving the pivot connection with said handle portions, and thereby accommodate the pivoting of said handles.

9. An instrument for compression and distraction of objects comprising two elongated first and second handles, a pivot pin pivotally connecting said handles together at a location intermediate the length of said handles, said handles being arranged to each have hand-grip portions thereon disposed to one side of said pivot pin and to have jaw portions thereon to the side of said pivot pin opposite from said one side whereby said jaw portions move toward and away from each other when said hand-grip portions are respectively moved toward and away from each other, a first additional jaw pivotally connected to said hand-grip portion of said first handle and pivotally connected to said jaw portion of said second handle, and with those two pivot connections being on opposite sides of and equally spaced from said pivot pin, and a second additional jaw pivotally connected to said hand-grip portion of said second handle and pivotally connected to said jaw portion of said first handle, and with those two pivot connections being on opposite sides of and equally spaced from said pivot pin, and with each of said additional jaws having distal ends extending away from said pivot pin to a location beyond said jaw portions for engagement of objects, each of said distals ends having surfaces on each opposite side thereof for engagement of objects in the respective compression and distraction of said objects, said pivot pin and said pivot connections of each of said additional jaws being connected to said handles in positions to form a straight line along said connections and said pivot pin and to accommodate pivoting of said handles about said pivot pin, a screw supported relative to said pivot pin and extending between said handles, a nut threadedly mounted on said screw and being movable therealong upon turning of said screw, and a lever pivotally connected with said nut and each of said hand-grip portions and arranged to move said hand-grip portions toward and away from each other upon turning of said screw for either compression or distraction of objects.

10. The instrument for compression and distraction of objects as claimed in claim 9, wherein said additional jaws are disposed parallel to each other and being arranged for both compression and distraction.

11. The instrument for compression and distraction of objects as claimed in claim 10, wherein said additional jaws are arranged to have said connections in each of said additional jaws move in equal amounts of movement upon pivoting of said handles and thereby remain parallel to each other throughout the pivoting of said handles.

12. The instrument for compression and distraction of objects as claimed in claim 10, wherein said additional jaws each have a straight slot therein for receiving the pivot connection with said handle portions, and thereby accommodate the pivoting of said handles.

13. The instrument for compression and distraction of objects as claimed in claim 9 including the portions of said additional jaws extending away from said pivot pin having surfaces on each opposite side of each of said additional jaws for the said engagement of objects in a selective a compression or distraction force on said objects.

14. The instrument for compression and distraction of objects as claimed in claim 13, wherein all said surfaces on said additional jaws are disposed parallel to each other.

15. The instrument for compression and distraction of objects as claimed in claim 9, including an anti-friction connection interconnected between said screw and said pivot pin for connecting said screw to said pivot pin.

16. The instrument for compression and distraction of objects as claimed in claim 15, including a lubrication pocket disposed at said anti-friction connection for receiving lubrication for the interconnection between said screw and said pivot pin.

17. The instrument for compression and distraction of objects as claimed in claim 15, wherein said anti-friction connection is a thrust type of bearing connection arranged to receive the thrust of said screw exerted onto the pivot pin.

18. An instrument for compression and distraction of objects comprising two elongated first and second handles, a pivot pin pivotally connecting said handles together at a location intermediate the length of said handles, said handles being arranged to each have hand-grip portions thereon disposed to one side of said pivot pin and to have jaw portions thereon to the side of said pivot pin opposite from said one side whereby said jaw portions move toward and away from each other when said hand-grip portions are respectively moved toward and away from each other, a first additional jaw pivotally connected to said hand-grip portion of said first handle and pivotally connected to said jaw portion of said second handle, and with those two pivot connections being on opposite sides of and equally spaced from said pivot pin, and a second additional jaw pivotally connected to said hand-grip portion of said second handle and pivotally connected to said jaw portion of said first handle, and with those two pivot connections being on opposite sides of and equally spaced from said pivot pin, and with each of said additional jaws extending away from said pivot pin to a location beyond said jaw portions for engagement of objects, a screw pivotally attached to said hand-grip portion of said first one of said handles and extending to said hand-portion of said second one of said handles, and a nut on said screw and engaged with said hand-grip portion of said second one of said handles and being connected thereto for movement of said hand-grip of said second handle in both directions along the extent of said screw, and being in an arrangement whereby turning of said screw causes said nut to move along said screw and thereby move said hand-grip portions toward or away from each other.

19. The instrument for compression and distraction of objects as claimed in claim 18, wherein said nut is releasably connected to said second handle and said handles lie along one common plane and the axis of pivot of said screw on said first handle is transverse to to said plane for folding of said screw relative to said handles and in said plane when said nut is released from said second handle.

20. The instrument for compression and distraction of objects as claimed in claim 19, wherein said second handle has a slot thereon for receiving said nut and with said slot being aligned for movement of said nut from said slot when said screw is pivoted in said plane.

21. The instrument for compression and distraction of objects as claimed in claim 20, wherein said pivotal connection of said screw with said first handle includes pivotal clearance of said screw relative to said first handle in an arrangement whereby said screw can pivot approximately three-quarters of a circle from an operative position of forcing on said second handle to an inoperative position extending parallel and alongside said first handle.

22. The instrument for compression and distraction of objects as claimed in claim 18, including said handles being arranged to be pivotal in a plane which is transverse to the axis of said pivot pin, and said screw being arranged to be pivotal along said plane, said hand-grip portion of said second handle including two spaced-apart fingers arranged to present a slotted opening extending on said plane, said nut being of a size sufficient to be disposed between said fingers and into and out of said slotted opening when said screw is pivoted along said plane, and said fingers and said nut having mutually engageable surfaces disposed for engagement in response to movement of said nut upon rotation of said screw in both directions about its longitudinal axis, to thereby move said hand-grip portions toward and away from each other in both directions of operation upon rotation of said screw.

23. The instrument for compression and distraction of objects as claimed in claim 22, wherein said mutually engageable surfaces are arranged to non-rotatably engage each other whereby said nut is restrained from rotating when said screw is rotated, and said nut therefore can move only axially of said screw.

24. An instrument for compression and distraction of objects comprising:

a pair of pivotally connected handles having a pivot axis and having hand-grip portions to one side of said pivot axis and having jaw portions to the other side of said pivot axis, two pairs of surfaces on said jaw portions for gripping work-piece objects and with said surfaces of a first one of said pairs facing each other and with said surfaces of a second one of said pairs facing away from each other, with said first and said second pairs being arranged for respective compression and distraction of the work-piece objects, a screw pivotally connected with said handles and having a longitudinal axis, a nut threadedly mounted on said screw and being connected to said handles in an arrangement to be restrained from rotation and thereby induce movement of said nut along said axis of said screw in both directions therealong and upon rotation of said screw, and said nut being operatively connected to said handles to transmit the movement of said nut along said screw in both said directions and to said hand-grip portions to achieve the compression and distraction operation.

25. The instrument for compression and distraction of objects as claimed in claim 24, including links pivotally connected between said nut and said hand-grip portions for the transmitting of the movement of said nut to said hand-grip portions.

26. The instrument for compression and distraction of objects as claimed in claim 24, including said screw being pivotally connected to said hand-grip portion of a first one of said handles and extending to said hand-grip portion of a second one of said handles, and said nut having two oppositely facing surfaces arranged for respective contact with said hand-grip portion of said second handle for transmitting said both directions of movement of said nut to said handles upon rotation of said screw.

27. The instrument for compression and distraction of objects as claimed in claim 26, wherein said screw is pivotally connected to said first handle with sufficient clearance therewith to pivot in a total of three-quarters of a circle about the pivot axis of the connection, to thereby be positioned adjacent said hand-grip portion of said second handle, in a position of operation, and to thereby be positioned to extend along side and adjacent to said first handle, in a non-operative position.

* * * * *